US010443881B2

(12) United States Patent
Cubizolles et al.

(10) Patent No.: US 10,443,881 B2
(45) Date of Patent: Oct. 15, 2019

(54) METHOD FOR CONTROLLING A FAN

(71) Applicant: SEB S.A., Ecully (FR)

(72) Inventors: Serge Cubizolles, Oytier Saint Oblas (FR); Belkacem Aberbache, Rumilly (FR); Olivier Lavillat, Quintal (FR)

(73) Assignee: SEB S.A., Ecully (FR)

( * ) Notice: Subject to any disclaimer, the term of this patent is extended or adjusted under 35 U.S.C. 154(b) by 314 days.

(21) Appl. No.: 15/311,059

(22) PCT Filed: May 12, 2015

(86) PCT No.: PCT/FR2015/051243
§ 371 (c)(1),
(2) Date: Nov. 14, 2016

(87) PCT Pub. No.: WO2015/173509
PCT Pub. Date: Nov. 19, 2015

(65) Prior Publication Data
US 2017/0108237 A1  Apr. 20, 2017

(30) Foreign Application Priority Data
May 14, 2014  (FR) ...................... 14 54306

(51) Int. Cl.
F24F 11/00 (2018.01)
F04D 25/08 (2006.01)
(Continued)

(52) U.S. Cl.
CPC ............ F24F 11/77 (2018.01); F04D 25/088 (2013.01); F04D 27/004 (2013.01); F04D 29/705 (2013.01); F24F 6/00 (2013.01); F24F 7/007 (2013.01); F24F 13/078 (2013.01); G08C 17/02 (2013.01); F24F 11/52 (2018.01);
(Continued)

(58) Field of Classification Search
CPC .... F04D 25/088; F04D 27/004; F04D 29/705; F24F 6/00; F24F 7/007; F24F 11/52; F24F 11/56; F24F 11/58; F24F 11/77; F24F 11/0079; F24F 2003/1689; F24F 2011/0064; F24F 2011/0068; F24F 2011/0071; F24F 2011/0091; F24F 2221/02; G08C 17/02
See application file for complete search history.

(56) References Cited

U.S. PATENT DOCUMENTS 4,711,161 A   12/1987  Swin, Sr. et al.
4,719,446 A   1/1988   Hart
(Continued)

Primary Examiner — Igor Kershteyn
(74) Attorney, Agent, or Firm — The Webb Law Firm

(57) ABSTRACT

Provided is a method for controlling a fan (1) which includes a control unit (2), wherein the control method includes at least the following steps: —the selection of an operating program (22) of the fan (1) from among a plurality of operating programs pre-recorded in the control unit (2), the operating programs including at least first and second fan control data; and the sending, by the control unit (2), of a control signal including at least the first control data for controlling a motor, which are correlated with at least the second control data for controlling at least one secondary device (24) of the fan (1) selected from among: a lighting device; a gas or liquid spraying device; an acoustic device; and a video device.

12 Claims, 3 Drawing Sheets

(51) Int. Cl.
- *F04D 27/00* (2006.01)
- *F04D 29/70* (2006.01)
- *F24F 6/00* (2006.01)
- *F24F 7/007* (2006.01)
- *F24F 11/77* (2018.01)
- *F24F 13/078* (2006.01)
- *G08C 17/02* (2006.01)
- *F24F 3/16* (2006.01)
- *F24F 11/65* (2018.01)
- *F24F 11/56* (2018.01)
- *F24F 11/52* (2018.01)
- *F24F 11/58* (2018.01)

(52) U.S. Cl.
CPC ............. *F24F 11/56* (2018.01); *F24F 11/58* (2018.01); *F24F 11/65* (2018.01); *F24F 2003/1689* (2013.01); *F24F 2221/02* (2013.01)

(56) References Cited

U.S. PATENT DOCUMENTS

| | | | |
|---|---|---|---|
| 4,818,920 A | 4/1989 | Jacob | |
| 5,189,412 A | 2/1993 | Mehta et al. | |
| 5,365,154 A * | 11/1994 | Schneider | G05B 19/0423 307/115 |
| 5,528,229 A | 6/1996 | Mehta | |
| 5,791,763 A | 8/1998 | Kam-Hoi | |
| 5,909,087 A * | 6/1999 | Bryde | H05B 37/0263 315/149 |
| 7,521,872 B2 * | 4/2009 | Bruning | H05B 33/0821 315/149 |
| 8,123,381 B1 * | 2/2012 | Wray | F21V 23/005 362/294 |
| 2008/0025028 A1 * | 1/2008 | Gloisten | F21V 5/04 362/294 |
| 2009/0040470 A1 * | 2/2009 | Fukui | G03B 21/16 353/58 |
| 2012/0033419 A1 | 2/2012 | Kim et al. | |

* cited by examiner

METHOD FOR CONTROLLING A FAN

CROSS-REFERENCE TO RELATED APPLICATIONS

This application is the United States national phase of International Application No. PCT/FR2015/051243 filed May 12, 2015, and claims priority to French Patent Application No. 1454306 filed May 14, 2014, the disclosures of which are hereby incorporated in their entirety by reference.

FIELD OF THE INVENTION

The invention generally concerns a fan, which acts on the air in a residential room.

More specifically, the invention concerns a fan that operates according to pre-recorded programs.

DESCRIPTION OF RELATED ART

In another field, the document US2012033419 discloses an optical lighting device with semiconductors to generate ambient light and including ventilation of the components.

Fans are known that are equipped with a control unit that operates means of ventilation integrated into the fan. For example, the control unit enables operation of the means of ventilation at several operating speeds. In another example, the control unit enables operation of the means of ventilation in one direction of rotation or another. Some fans include means of lighting in parallel to the means of ventilation, which can also be controlled by the control unit.

Accordingly, document U.S. Pat. No. 5,528,229 describes a fan which is adapted to be attached to the ceiling of a residential room. It includes means of ventilation, means of lighting and a temperature sensor. The fan includes a control unit which makes it possible to control the assembly, and this control unit includes one or more operating programs. A first operating program permits activation of the means of ventilation at different speeds or in one particular direction of rotation. In addition, in this operating program, the temperature of a residential room is measured by the temperature sensor and the speed of the means of ventilation is adjusted to cool or evenly distribute the temperature of the residential room. Therefore, this makes it possible to regulate the temperature of the habitable room, and this regulation is automatic based on the operating program selected, which includes pre-recorded temperature instructions. The control unit also includes a second operating program for the means of lighting. This second operating program manages the illumination from the means of lighting. However, lighting operations are basic operations on the luminaire such as, for example, switching on, switching off or controlling the intensity of the luminaire according to a defined plan and graduated intensity values. In this document, the means of ventilation and lighting function independently.

One of the inconveniences of this type of fan resides in the fact that the control unit must have at least two different control systems in order to control the lighting and ventilation separately according to the operating programs selected. This has an impact on the cost of the system. One of the objectives of the present invention is to offer a device that is less expensive by simplifying the control scheme.

Another inconvenience is that the functions offered by such a fan are limited to either ventilation only or lighting only. Another objective of the present invention is therefore to offer a fan that includes the combined functions of ventilation and lighting, as well as additional functions.

Yet another inconvenience resides in the fact that the ventilation and lighting function through independent programs, which does not make this type of fan easy to use, because it requires starting the lighting and the ventilation separately. Another objective of this invention is therefore to offer a method for use of a fan that makes it possible to start all the functions of the fan at the same time and in a dependent manner, without multiplying the interactions with the control unit.

SUMMARY OF THE INVENTION

To achieve this objective, the invention concerns a fan control method which includes a control unit, and the control method is characterized in that it includes at least the following steps:

Selection of an operating program for the fan from among multiple operating programs pre-recorded in the control unit, and the operating programs include at least the first and second fan control data;

And emission by the control unit of a control signal including at least the first control data to control a motor, which are correlated with at least the second control data to control at least one secondary device of the fan chosen from among:

A lighting device;
A gas or liquid spraying device;
An acoustic device;
A video device.

According to the invention, the control method of the fan also includes, between the step to select the operating program and the step to emit the single control signal mentioned previously, a step to retrieve the control data, which is carried out by a processor integrated into the control unit, which consists of retrieving, in a memory integrated into the control unit, the first control data and, at least, the second control data based on the operating program selected, and a step to compile these control data, which consists of performing logical operations on these control data in order to correlate these control data and integrate them into the control signal.

The invention also concerns a fan that uses the control method described previously.

According to the invention, the fan includes:
a control unit that includes a selection interface for the operating program pre-recorded in the control unit;
the control unit has a memory where at least the first control data to control the motor and at least the second control data to control at least one secondary device of the fan are stored, and the secondary device of the fan is selected from among the following:
A lighting device;
A gas or liquid spraying device;
An acoustic device;
A video device;
the control unit has a processor that can access the memory and retrieve control data to control the motor and at least the second control data related to the program selected and compile these control data.

According to the invention, the lighting device of the fan consists of one or more white light-emitting diodes, which form a luminaire whose total power is 3-150 Watts.

Still according to the invention, the lighting device of the fan consists of one or more color light-emitting diodes, which form a luminaire whose total power is 3-150 Watts.

According to the invention, the fan motor is a brushless motor and it is integrated into a device that comprises fan blades.

According to one embodiment of the invention, the control unit of the fan is placed away from the fan and includes a wireless device to transmit and receive control data.

According to the invention, the fan includes a wireless device to transmit and receive control data and an internal memory to store these control data.

According to the invention, the wireless device to transmit and receive control data from the control unit and the wireless device to transmit and receive control data from the fan communicate with each other through radio frequency signals.

According to the invention, the fan can communicate with a remote module connected to the internet.

According to the invention, the control unit can communicate with a remote module connected to the internet.

And still according to the invention, the fan's internal memory can be programmed remotely.

BRIEF DESCRIPTION OF THE DRAWINGS

Other characteristics and advantages of the present invention will appear more clearly when reading the detailed description, which follows an embodiment of the invention provided as a non-limiting example and illustrated by the attached drawings, in which.

DETAILED DESCRIPTION OF THE INVENTION

Figure 1:
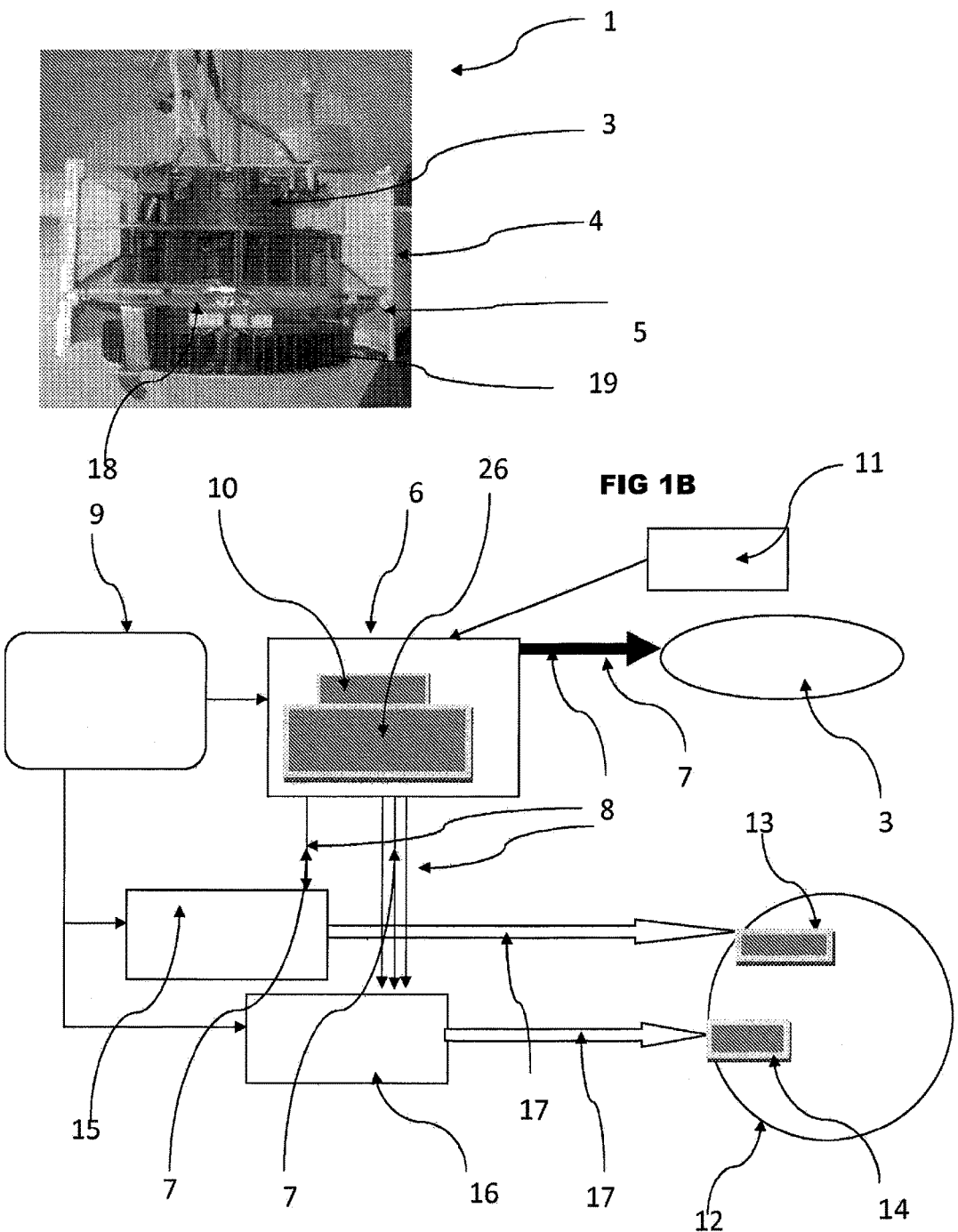
FIG. 1A is a cross-sectional view of a fan according to the invention.
FIG. 1B is an overview diagram of the electronics of the fan according to the invention.

As can be seen in FIG. 1A or 1B a fan (1) according to the invention has a motor (3) and the motor (3) is integrated into a device (4) that comprises fan blades (5). In a preferred embodiment, this motor (3) is a brushless motor (3).

The fan (1) also includes an electronic operation and control card (6). This electronic card (6) is connected to the motor (3) and permits at least speed and rotation control of the motor (3).

This control of the motor (3) is obtained through modulation of the pulse width (7), and an H-bridge electronic structure (8) is used between the motor (3) and the electronic operation card (6).

The fan (1) includes a mains power supply (9) which operates at 120-230 Volt and at frequencies ranging from 50-60 Hz.

The fan (1) also includes a wireless data receiving device (10). This device (10) is connected to the electronic operation card (6) and can be located either in the electronic operation card (6) or separate from it.

The wireless data receiving device (10) is adjusted to receive radio frequency data, and it can also transmit data.

A temperature sensor (11) is connected to the electronic operation card (6).

The fan (1) also has a lighting device (12). This lighting device (12) is composed of one or more white light-emitting diodes (13) that form a luminaire whose total power is 3-150 Watts. This lighting device (12) can also consist of one or more color light-emitting diodes (14) that form a luminaire whose total power is 3-150 Watts. These color light-emitting diodes (14) are of the RGB (Red, Green, Blue) type, making it possible to obtain the entire spectrum of existing colors.

White light-emitting diodes (13) and color light-emitting diodes (14) can be positioned on the same luminaire.

The advantage of using light-emitting diodes (13, 14) is that consumption is lower than with a traditional bulb. The efficiency is better, and therefore heating is reduced.

More specifically, the supply to power light-emitting diodes (13, 14) is a switching power supply and this supply is delivered by direct current.

A 25 W switching power supply (15) is used for white light-emitting diodes (13) and a 10 W switching power supply (16) is used for RGB color light-emitting diodes (14).

The control for the light-emitting diodes (13, 14) is an isolated direct-current control (17).

The switching power supplies (15, 16) provide resistance to disturbances in the supply area such as lightning, voltage dips and static. The immunity of the light-emitting diodes (13, 14) to these disturbances is increased.

White light-emitting diodes (13) and color light-emitting diodes (14) are positioned in the fan (1) on a support block (18). Because of the elevated temperature due to the light-emitting diodes (13, 14), a cooling fin (19) is provided near the support block (18) to ensure thermal contact. This contact reduces the heat of the support block (18).

Figure 2:
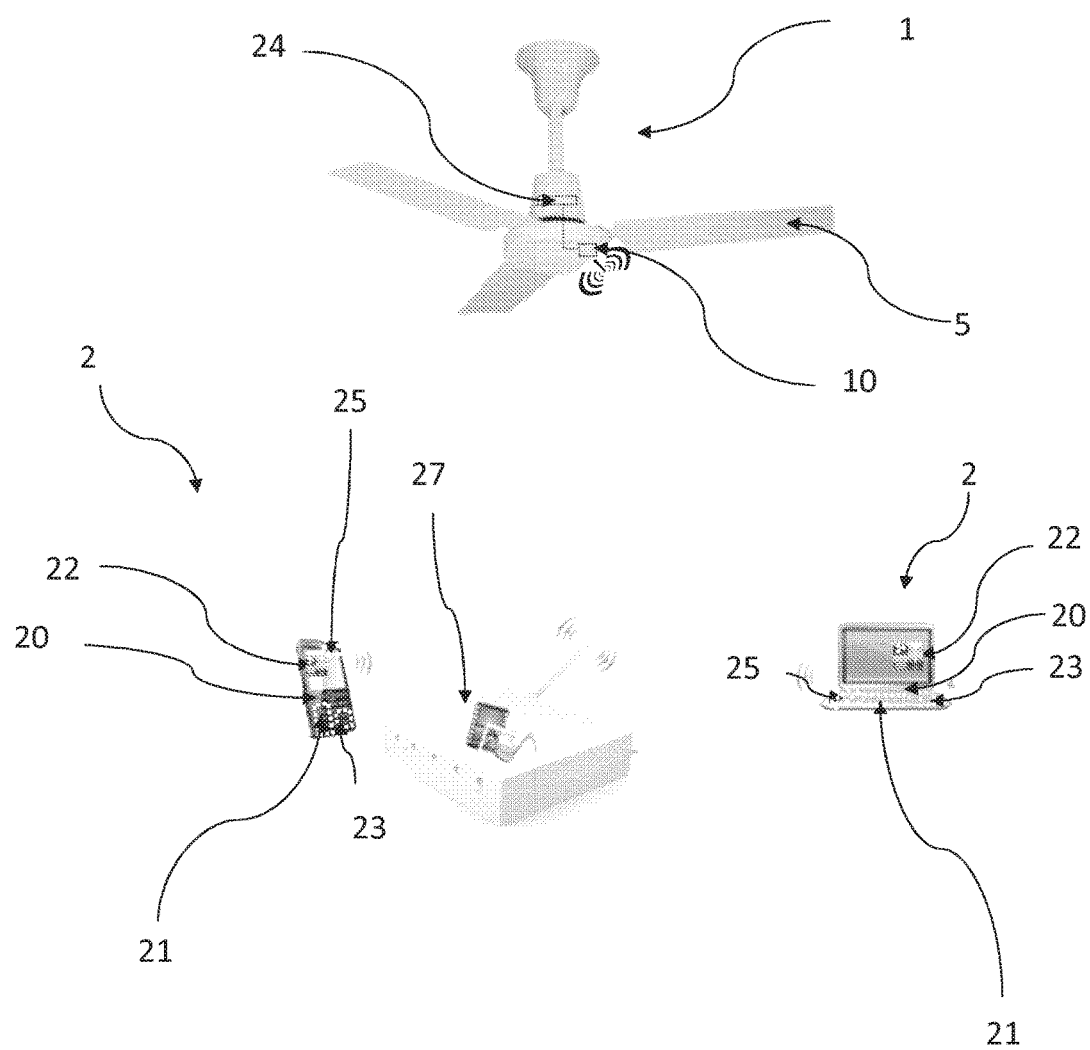
FIG. 2 is a perspective view of a fan according to the invention.

As shown in FIG. 2, the fan (1) includes a control unit (2). This control unit (2) includes a selection interface (20). This selection interface may be a capacitive or resistive touchscreen.

The control unit (2) has means of memorization (21) so that it can store pre-recorded operating programs (22) in the memory. These means of memorization (21) are available in the form of a memory. This memory (21) can be programmable.

The selection interface (20) enables the display of these operating programs (22), and pressing on it makes it possible to select one of the operating programs (22).

The operating programs (22) include at least the first control data to control the motor and at least the second control data to control at least one secondary device (24) of the fan (1).

In addition to the lighting device (12), the secondary device (24) of the fan (1) can be a gas or liquid spraying device, acoustic device or even a video device.

Gas or liquid spraying device should be understood to mean all devices that are able to spray gases, such as perfumes.

This gas or liquid spraying device can diffuse all sorts of scents or perfumes, and it can also vaporize liquids such as water.

The video device is a device that can project images or videos through an image or light projector.

The control unit (2) includes a processor (23) that can access the memory (21) and enables the retrieval of control data to control the motor (3) and, at least the second control data of the secondary device (24).

In the case where the control unit (2) of the fan (1) is placed apart from the fan (1), it includes a wireless transmission device (25) for control data.

The control unit (2) and the fan (1) communicate through radio frequency signals.

The electronic operation and control card (6) of the fan (1) includes an internal memory (26) and the operating programs (22) can be sent by the control unit (2) to the fan and stored in the internal memory (26) of the fan (1), still assuming the control unit (2) is placed apart from the fan (1).

The fan (1) or control unit (2) can also communicate with a remote module (27) connected to the internet.

This allows the operating programs (22) to be retrieved from the internet by the control unit (2) on the control unit's memory (21) or the fan's internal memory (26).

The control unit (2) can be a remote control with a screen, a tablet or a smartphone. It can also be a mainframe computer or television.

Figure 3:
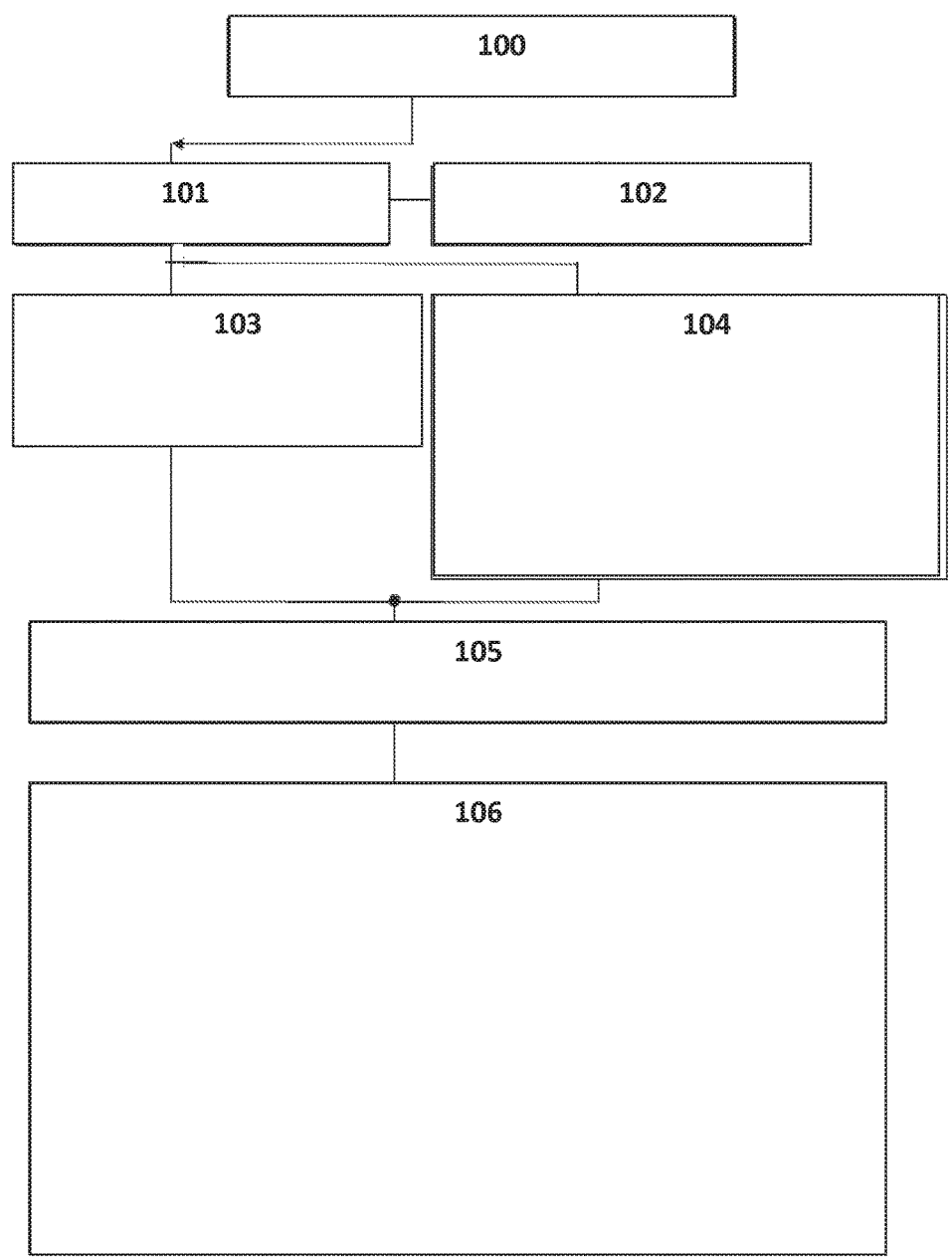
FIG. 3 is a logic diagram of the method of use of a fan according to the invention.

As shown in FIG. 3, the fan (1) operates in the following manner:

The fan (1) is powered up in a startup step (100).

In the next step (101), the control unit (2) is also powered up and the operating programs (22) are displayed on its interface (20).

During this step (101), the fan (1) communicates with the control unit (2) and they are paired together.

In another operation step (102), when the control unit (2) is turned on, it is paired with a remote module (27) connected directly to the internet. This allows the control unit (2) to retrieve operating programs (22) on the internet.

In a subsequent selection step (103), a pre-programmed operating program is selected on the control unit (2).

In one embodiment, it is possible to proceed to a programming step (104) for the operating program (22). This is a personalized operating program (22) in which control data are input manually in the form of parameters. Accordingly, parameters such as the length of operation, date and time of activation, luminous intensity, color of the lighting device, variation of light from the lighting device, operating speed of the ventilation device, variation of ventilation, temperature instructions, scent or gas diffusion instructions, image projection and sound transmission can be found.

After the selection (103) or programming (104) steps of the operating program (22) are carried out, the control data are communicated or transmitted to the fan (1) and stored in the fan's internal memory (26) during a transmission step (105).

Control data are transmitted to the fan (1) in the form of a control signal in which the first control data to control the motor (3) are correlated with the second control data to control the fan's (1) secondary device (24).

Correlated data means that the first control data are not independent of the second control data, rather they are related to each other insofar as a specific second control data value to control the fan's secondary device will be associated with a specific first control data value to control the fan. The control signal will therefore transport these two related sets of information together.

This correlation or correspondence between the first and second control data is established directly in the pre-recorded operating program(s) selected. Diagrams of correlation between the control data are pre-recorded in them in the form of computerized tables or databases.

These operations will be performed by the processor (23) integrated into the control unit, which will compile these control data, which will consist of performing logic operations on these control data in order to obtain from them correlated data and then integrate them into the control signal, which is unique insofar as a single signal transmits all the control data.

For example, a diode color will be associated with a specific rotation speed of the motor.

These operating programs also include time information. This time information corresponds to a period which defines the time during which the control signal including the first and second control data will be transmitted.

As in the previous example, the time information included in the programs will enable a particular rotation speed for the motor correlated with a specific color of the diodes only during a defined period, then at the end of that period, the program either stops sending the control signal or transmits another control signal with another specific rotation speed for the motor correlated with another specific color of the diodes, and this also for another period of time, which may be different from the first, and so on.

These data are transmitted to the fan by radio frequency signals. The fan (1) can also receive information from the temperature sensor (11) in this transmission step (105).

Once all the information and control data are received by the electronic operation card (6), there is a fan (1) control step (106) that ensures automatic control of its operation based on the control data and information received.

In this operation step (106), the fan (1) can also send information to the control unit (2).

It is understood that various modifications and/or improvements obvious to persons skilled in the art may be made to the embodiment of the invention described in this description without going beyond the scope of the invention defined by the appended claims.

The invention claimed is:

1. A method for controlling a fan that includes providing a control unit wherein the control method includes at least the following steps:
   (A.) selecting an operating program for the fan from among multiple operating programs pre-recorded in a control unit, and the operating programs include at least a first and second control data for the fan; and
   (B.) transmitting by the control unit of a control signal including, at least, the first control data to control a motor, which are correlated with, at least, the second control data to control, at least, a secondary device of the fan, selected from among the following: a lighting device; a gas or liquid spraying device; an acoustic device; and a video device.

2. The method for controlling a fan according to claim 1, wherein the control method also includes, between the aforementioned operating program selection step (A.) and single control data transmission step (B.), a control data retrieval step, performed by a processor integrated into the control unit, which consists of retrieving, in a memory integrated into the control unit, the first control data and, at least, the second control data based on the operating program selected, and a step of compiling these control data, which consists of performing logic operations on these control data in order to correlate the control data and integrate the control data into the control signal.

3. A fan using the control method according to claim 1, wherein the fan includes:
   a control unit, which includes an interface to select an operating program pre-recorded in the control unit; and wherein the control unit has a memory wherein are stored, at least, the first control data to pilot a motor and, at least, the second control data to pilot, at least, one secondary device of the fan, and wherein the secondary device of the fan is selected from among the following: a lighting device; a gas or liquid spraying device; an acoustic device; and a video device;
   and wherein the control unit has a processor, which accesses the memory and retrieves the control data to pilot the motor and, at least, the second control data related to the program selected and to compile the control data to obtain a control signal in which the data are correlated.

4. The fan according to claim 3, wherein the lighting device includes one or more white light-emitting diodes, which form a luminaire whose total power is 3-150 Watts.

5. The fan according to claim 3, wherein the lighting device includes one or more color light-emitting diodes, which form a luminaire whose total power is 3-150 Watts.

6. The fan according to claim 3, wherein the motor is a brushless motor and is integrated into a device comprising fan blades.

7. The fan according to claim 3, wherein the control unit is located away from the fan and includes a wireless control data transmission and receiving device.

8. The fan according to claim 7, wherein the wireless control data transmission and receiving device includes an internal memory to store the control data.

9. The fan according to claim 8, wherein the wireless control data transmission and receiving device of the control unit and the wireless control data transmission and receiving device of the fan communicate with each other using radio frequency signals.

10. The fan according to claim 3, wherein the fan communicates with a remote module connected to the internet.

11. The fan according to claim 3, wherein the control unit communicates with a remote module connected to the internet.

12. The fan according to claim 3, wherein the fan has an internal memory that can be programmed remotely.

\* \* \* \* \*